United States Patent [19]

Kratochwilla

[11] Patent Number: 4,470,163
[45] Date of Patent: Sep. 11, 1984

[54] SPITTING DEVICE FOR DENTAL PURPOSES

[75] Inventor: Hans M. Kratochwilla, Lorsch, Fed. Rep. of Germany

[73] Assignee: Siemens Aktiengesellschaft, Berlin & Munich, Fed. Rep. of Germany

[21] Appl. No.: 508,885

[22] Filed: Jun. 29, 1983

[30] Foreign Application Priority Data

Jun. 30, 1982 [DE] Fed. Rep. of Germany ....... 3224488

[51] Int. Cl.$^3$ .............................................. A61C 17/04
[52] U.S. Cl. .......................................... 4/263; 4/262
[58] Field of Search .................. 4/263, 262, 264, 266, 4/265, 661, 266

[56] References Cited

U.S. PATENT DOCUMENTS

| | | | |
|---|---|---|---|
| 710,638 | 10/1902 | Van Nostran | 4/263 |
| 793,134 | 6/1905 | Hughes | 4/263 |
| 3,281,868 | 11/1966 | McGouirk | 4/263 |
| 3,359,575 | 12/1967 | Nielsen | 4/263 |
| 3,653,078 | 4/1972 | Buchtel et al. | 4/263 |
| 3,790,971 | 2/1974 | Fox | 4/263 |

FOREIGN PATENT DOCUMENTS 1808006 3/1980 Fed. Rep. of Germany .

OTHER PUBLICATIONS

Siemens Brochure M-D 1p/1268, Entitled "Für Ihre Helferin: Wassereinheit SIRO1 oder SIRO 2".

Primary Examiner—Henry K. Artis
Attorney, Agent, or Firm—Hill, Van Santen, Steadman & Simpson

[57] ABSTRACT

A cuspidor or spitting device for dental purposes comprising a bowl formed by a lateral curved wall and a conical bottom surface with the upper edge of the lateral curved wall merging with an inclined surface portion of the upper surface of the housing and the bottom wall having a discharge opening leading to a discharge channel. The lateral wall is preferably a cylinder or a tapering surface substantially forming a cylinder whose axis of rotation is arranged to incline from the user's side and forms an acute angle with the axis of the conical surface forming the bottom wall. Thus, the surfaces are smooth and easily cleaned and do not provide cracks or crevices for accumulation of dirt and prevent anti-hygienic conditions from occurring.

10 Claims, 4 Drawing Figures

SPITTING DEVICE FOR DENTAL PURPOSES

BACKGROUND OF THE INVENTION

The present invention is directed to a spitting device or cuspidor for use in dental purposes. The cuspidor or device has an upper planar surface which slopes toward one side which is adjacent the user and has a bowl disposed in the planar surface with its upper rim lying in or merging with the planar portion. In addition, a bottom wall of the bowl will have a discharge opening which leads to a discharge channel and the cuspidor or device includes a rinsing water outlet for discharging rinsing water or fluid into the bowl.

Examples of cuspidors or spitting devices are disclosed by German Utility Model No. 1,808,006 and Siemens Brochure M-D 10/1268, entitled "Für Ihre Helferin: Wassereinheit SIRO 1 oder SIRO 2". In these disclosed devices, the upper bowl edge is designed in the form of a so-called overflow rim with which, for example, in the case of excessively strong rinsing, the rim will prevent the rinsing water from spraying over the rim of the bowl. Such an overflow rim, indeed, forms soil rims which are not visible from the exterior but which are not acceptable from a hygienic point of view. An additional problem is that rinsing water guidance, which in the case of known cuspidors or spitting bowls, is not yet satisfactory. The problem is that the walls cannot be kept sufficiently clean; they can only be kept sufficiently clean with a relatively great amount of water or the spitting bowl or cuspidor, for structural reasons, does not sufficiently correspond to the hygienic demands.

SUMMARY OF THE INVENTION

The present invention is directed to providing a spitting device or cuspidor having an upper surface with a bowl, which device or cuspidor better corresponds to the demands of hygiene and is thus easier to clean and avoids the collection of soil on the walls particularly during a rinsing operation. Thus, the bowl exhibits a better rinsing water guidance and due to structural features has fewer possible soilage rims.

In order to solve these objects, the invention is directed to a spitting device or cuspidor for dental purposes comprising an upper surface having a planar portion sloping toward one side of the device, said one side being the side closest to the user, a bowl having a lateral wall with an upper edge merging flush to said upper surface and lying in said plane portion and a lower edge merging with an upper edge of a bottom wall having a discharge opening, said lateral wall being a surface of revolution of a substantially straight line around a first axis, said first axis being inclined away from the one side, said straight line being substantially parallel to the first axis to form a surface of revolutions having a configuration which is substantially like a cylinder, said bottom wall being a conical surface with an apex around a second axis forming an acute angle to the first axis and having the opening arranged at the apex, and a rinsing water outlet for discharging into the bowl.

Preferably, due to the angle of the first axis relative to the axis of the conical bottom wall, the conical bottom wall has a portion adjacent the one side which is substantially larger than the portion opposite to the one side and thus, the apex and discharge opening are eccentrically arranged with respect to the area of the surface. In addition, the rinse water outlet preferably is a tubular member having a tubular portion extending at an angle of 30° relative to the horizontal line and discharging onto the narrow base surface. Preferably, the bowl, upper surface and sides of the device are an integrally formed member and the planar portion in addition to sloping toward the one side also slopes toward one corner so that any liquid on said planar portion runs into the bowl. The planar portion also adjacent the upper corner diametrically opposite to the one corner has a base depression for receiving and supporting a drinking glass. The base depression has a slight incline which slopes toward the one side of the device so that any liquid on this base will go onto the planar portion and eventually flow into the bowl. The upper surface on the two sides adjacent the one side has integral rims which extend into a rim on the one side to prevent overflowing. Preferably, the housing has a rectangular configuration with rounded corners and is arranged to set on a frame which also supports soil pipes or discharge channels as well as water inlet channels for rinsing and for filling a cup or glass.

DESCRIPTION OF THE PREFERRED EMBODIMENTS

Figure 1:
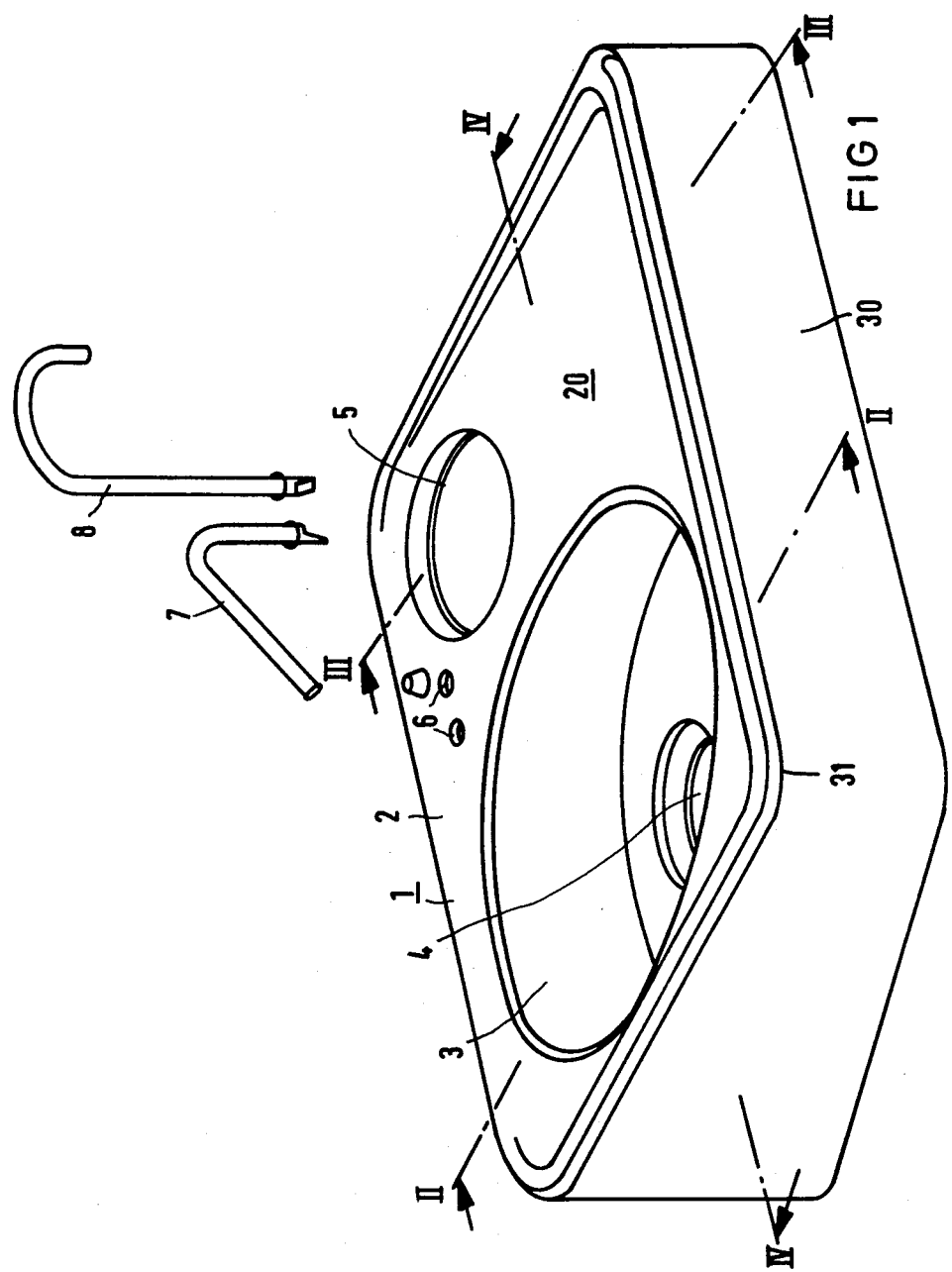
FIG. 1 is an exploded perspective view of a spitting device or cuspidor according to the present invention.

The principles of the present invention are particularly useful when incorporated in a spitting device or cuspidor having a housing 1 as illustrated in FIG. 1 which has a rectangular plan view with nicely rounded corners that merge with lateral edges. The housing 1 has an upper surface 2 which is substantially planar and slopes toward a side 30 as well as sloping slightly toward the corner 31 of the side 30. The side 30 is the side which will be closest to the user. The housing 1, which is preferably integrally formed, has a bowl-shaped recess 3 with a discharge opening 4. In addition, the planar portion of the upper surface 2 has a recess 5 which serves the purpose of receiving a drinking glass not illustrated in the drawing. The planar portion in the upper surface adjacent the bowl and the depression 5 has two holes 6. One hole receives a tube 7 which supplies a rinsing water into the bowl 3 and the other hole or aperture 6 receives a second tube 8 which serves the purpose for filling a glass placed in the recess 5.

Figure 2:
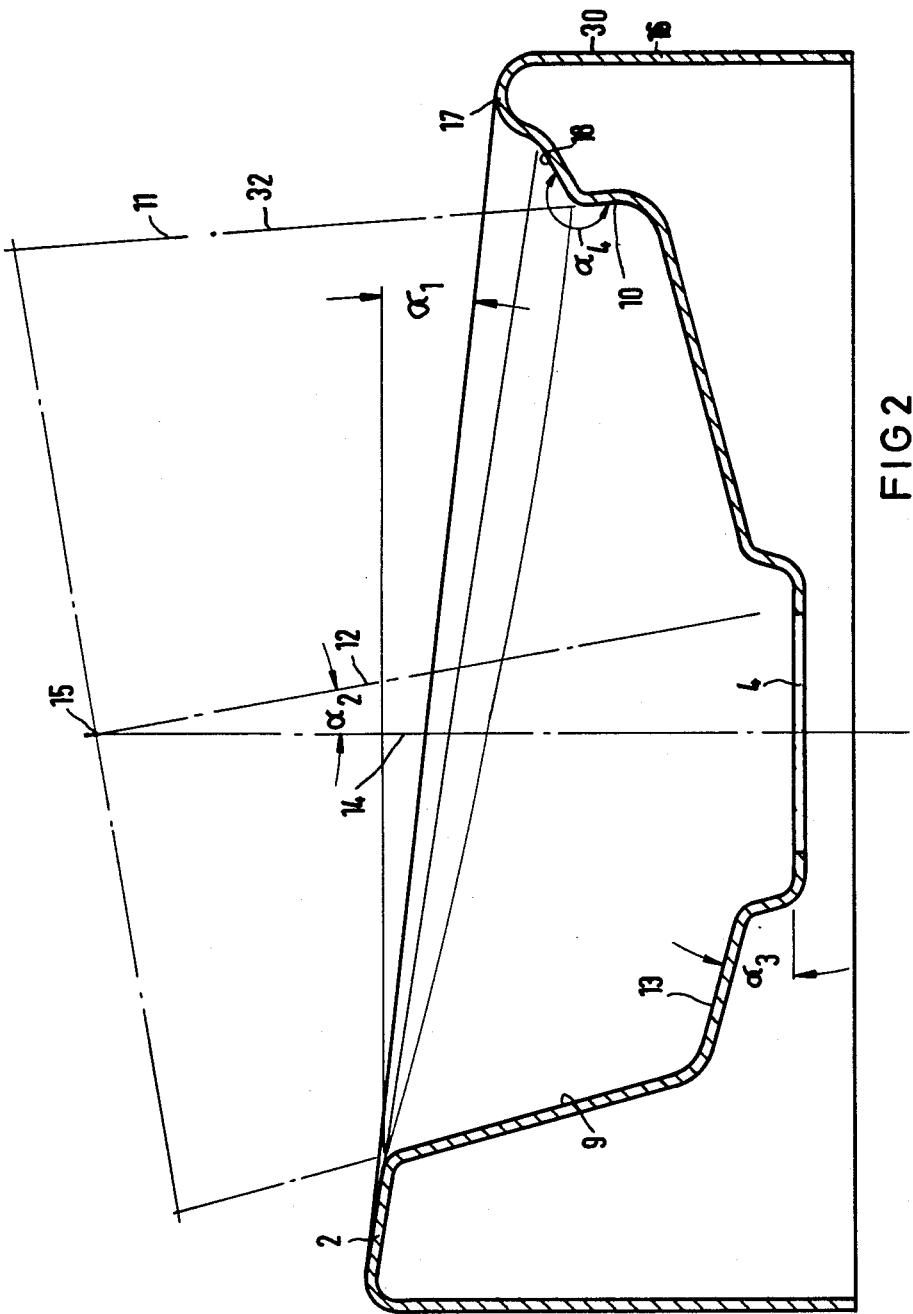
FIG. 2 is a cross-sectional view taken along the lines II—II of FIG. 1.

As best illustrated in FIG. 2, the planar surface 2 of the housing runs inclined or slopes in the direction of the user side 30 and is provided with a rim 17 which also slopes but not at the same angle and thus slopes at an angle $\alpha_1$ to the horizontal plane which angle $\alpha_1$ is in a range of 10° to 15°. The bowl 3 has a lateral wall formed by a surface revolution 11 which is formed by a substantially straight line 32 being rotated around a first axis 12 which is arranged at an angle $\alpha_2$ of 10° relative to a perpendicular line, namely, an axis 14. Thus, the first axis 12 slants or slopes away from the user's side 30. As illustrated, the surface of revolution 11 forms lateral walls 9 and 10 which due to the axis of the surface of revolution and the slope of the planar surface 2 have a different height. As illustrated, the liner 32 is almost parallel to the first axis 12 and thus forms a configuration which is substantially like a cylinder, however slightly tapering. The lateral walls such as 9 and 10 of the bowl 3 merge with a conical bottom wall or base 13 which has an apex and an axis 14 which is perpendicular to the horizontal plane and merges at point 15 with the first axis 12. The conical bottom wall forms an angle $\alpha 3$ with a horizontal plane which is approximately 15°. The cover surface 2 as well as the lateral and base walls 9, 10 and 13 have gentle transitions with a sufficiently large radius which enable easy cleaning of the surfaces. In the region of the user's side 1, the bead 17 merges with an exterior boundary wall 16 and also merges with a surface section 18 running at an obtuse angle $\alpha 4$ relative to the lateral wall portion 10. The outer edge of the surface section 18 merges flush into the planar portion 20 of the upper surface 2 (which is best shown in FIG. 3).

Figure 3:
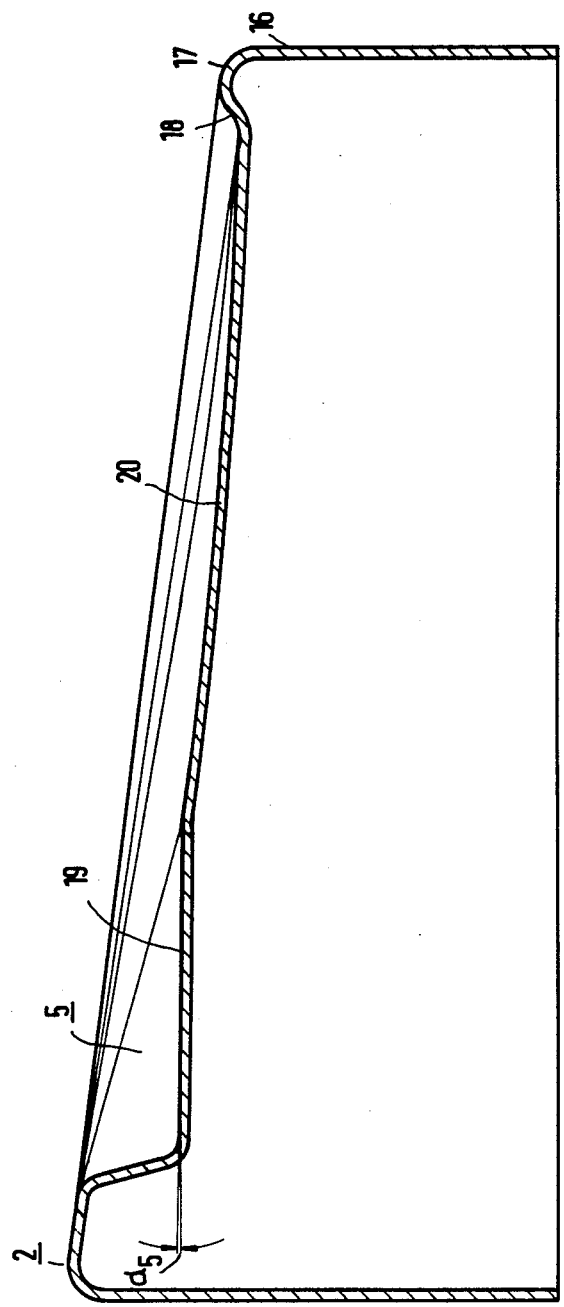
FIG. 3 is a cross-sectional view taken along the lines III—III of FIG. 1.

As best illustrated in FIG. 3, the base or depression 5 has a base surface 19 which is inclined at an angle $\alpha 5$ to the horizontal plane so that any water spillage on the base 19 will flow out onto the planar surface 20. As mentioned hereinabove, the planar surface 20 not only is inclined toward the one side 30 but also is inclined toward the corner 31 and that adjacent side so that any fluid thereon will flow into the bowl 3 to be removed through the single drainage opening 4.

Figure 4:
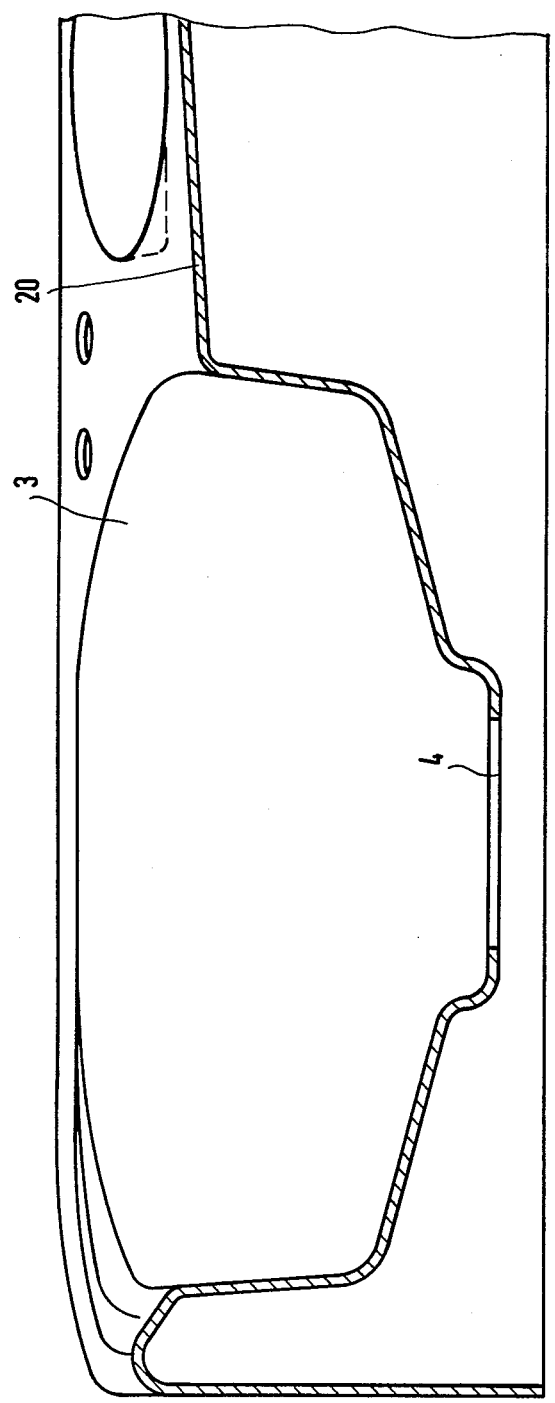
FIG. 4 is a cross-sectional view taken along the lines IV—IV of FIG. 1.

As is apparent from FIGS. 2 and 4, the drainage opening 4 is disposed eccentrically of the spitting bowl arrangement. The intake of the rinsing water as previously mentioned proceeds via tube 7 which is directed toward a lateral wall or base wall respectively and tangentially to point obliquely downward at an angle of approximately 30° relative to a horizontal line. Due to the previously described inclined bottom wall and the lateral walls, a spiral-shaped course for the rinsing water will occur with a rinsing water discharge location which is disposed opposite the widest rinsing surface and a discharge opening which is disposed at the end of the spiral of the rinsing water course. Thus, the rinsing water will sufficiently rinse the surfaces and can be discharged optimally without eddy formations.

Although various minor modifications may be suggested by those versed in the art, it should be understood that I wish to embody within the scope of the patent granted hereon, all such modifications as reasonably and properly come within the scope of my contribution to the art.

I claim:

1. A spitting device for dental purposes comprising a housing having an upper surface having a planar portion sloping toward one side of the device, said one side being the side closest to the user, a bowl having a lateral wall with an upper edge merging flush with the upper surface and a lower edge merging with an upper edge of a bottom wall having a discharge opening, said lateral wall having a surface of revolutions of a substantially straight line around a first axis, said first axis being inclined away from the one side and said straight line being substantially parallel to the first axis to form a surface of revolutions having a configuration substantially similar to a cylinder, said bottom wall being a conical surface with an apex and with a second axis forming an acute angle to the first axis and having the opening arranged at the apex, and a rinsing water outlet for discharging a rinsing water into the bowl.

2. A spitting device according to claim 1, wherein the configuration of the lateral wall and the merging bottom wall has the apex of the conical surface eccentrically disposed away from said one edge and the rinse water outlet comprises a tube extending into the bowl at an angle 30° to a horizontal plane for directing rinse water tangentially and obliquely downward on the side of the bowl adjacent the side of the housing opposite said one side.

3. A spitting device according to claim 2, wherein the housing is a one-piece member having a base formed in the planar surface portion for supporting a drinking glass.

4. A spitting device according to claim 3, wherein the planar surface portion slopes toward the bowl in addition to sloping toward one side so that water collected on the surface thereof discharges into the bowl.

5. A spitting device according to claim 4, wherein the base for the drinking glass is slightly inclined to a horizontal plane so that water spilled from the glass on the base will run onto the planar surface portion and drain into the bowl.

6. A spitting device according to claim 3, wherein said one side has an overflow rim extending therealong across the width of the housing, said overflow rim in the region of the bowl forming a bowl rim and terminating on the user's side with an exterior wall of the housing.

7. A spitting device according to claim 6, wherein the housing exhibits a rectangular cross-section and the rims are strongly rounded.

8. A spitting device according to claim 3, wherein the planar portion of the upper surface of the housing has two bores, one bore for receiving an inlet tube for the rinsing water outlet and the other bore for receiving an outlet tube for filling the drinking glass disposed on the base.

9. A spitting device according to claim 1, wherein said housing is a one-piece member with a rectangular configuration having rounded corners and side walls connected to the upper surface by rims.

10. A spitting device according to claim 9, wherein the rim on the one side forms an oveflow rim which adjacent the bowl forms a bowl rim.

* * * * *